US007875016B2

(12) United States Patent
Pahlberg et al.

(10) Patent No.: US 7,875,016 B2
(45) Date of Patent: Jan. 25, 2011

(54) FLEXIBLE MULTI-CHAMBER CONTAINER FOR THE PREPARATION OF MEDICAL MIXED SOLUTIONS

(75) Inventors: Olof Pahlberg, Bällinge (SE); Johan Engholm, Solna (SE); Manus O'Donnell, Hägersten (SE); Torsten Brandenburger, Niddatal (DE); Gerald Wegner, Rockenberg (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 11/658,899

(22) PCT Filed: Jun. 16, 2005

(86) PCT No.: PCT/EP2005/006474

§ 371 (c)(1),
(2), (4) Date: Jun. 11, 2007

(87) PCT Pub. No.: WO2006/010410

PCT Pub. Date: Feb. 2, 2006

(65) Prior Publication Data

US 2008/0004594 A1 Jan. 3, 2008

(30) Foreign Application Priority Data

Jul. 29, 2004 (EP) .................................. 04017922

(51) Int. Cl.
*A61B 19/00* (2006.01)

(52) U.S. Cl. ....................... 604/410; 604/408; 604/416; 604/403; 604/409

(58) Field of Classification Search ................. 604/409, 604/410, 416, 403, 408
See application file for complete search history.

(56) References Cited

U.S. PATENT DOCUMENTS 3,257,072 A * 6/1966 Reynolds ..................... 494/10

(Continued)

FOREIGN PATENT DOCUMENTS

CA 2393039 6/2001

(Continued)

OTHER PUBLICATIONS

International Search Report, for PCT/EP2005/006474, dated Nov. 4, 2005, 2 pages.

(Continued)

*Primary Examiner*—Tatyana Zalukaeva
*Assistant Examiner*—Susan Su
(74) *Attorney, Agent, or Firm*—Kenyon & Kenyon LLP

(57) ABSTRACT

A flexible multi-chamber container for preparation of medical mixed solutions includes at least three chambers separated from each other by leaktight seams. The chambers are designated to be filled with different solutions and are separated from each other by leaktight seams. At least a part of the first leaktight seam is provided with a separation zone to be opened for fluid transfer from the first chamber into the second chamber. At least a part of the second leaktight seam is provided with a separation zone to be opened for fluid transfer from the second chamber into the third chamber. The leaktight seams are arranged and the separation zones are formed such that, in use of the container for preparation of the medical mixed solution, the first separation and second separation zones are opened in a sequential order. The first zone is opened before the second separation zone is opened. Thus, the components are mixed one after another in a predetermined sequential order.

30 Claims, 6 Drawing Sheets

U.S. PATENT DOCUMENTS

| | | | | |
|---|---|---|---|---|
| 3,964,604 | A * | 6/1976 | Prenntzell | 206/219 |
| 4,331,264 | A * | 5/1982 | Staar | 222/94 |
| 4,396,383 | A * | 8/1983 | Hart | 604/518 |
| 4,465,488 | A * | 8/1984 | Richmond et al. | 604/414 |
| 4,484,920 | A * | 11/1984 | Kaufman et al. | 604/416 |
| 4,602,910 | A | 7/1986 | Larkin | |
| 4,759,472 | A | 7/1988 | Strenger | |
| 4,952,068 | A * | 8/1990 | Flint | 366/337 |
| 4,997,083 | A * | 3/1991 | Loretti et al. | 206/219 |
| 5,061,236 | A * | 10/1991 | Sutherland et al. | 604/6.09 |
| 5,195,658 | A * | 3/1993 | Hoshino | 222/92 |
| 5,209,347 | A * | 5/1993 | Fabisiewicz et al. | 206/219 |
| 5,263,609 | A | 11/1993 | Hoshino | |
| 5,431,496 | A * | 7/1995 | Balteau et al. | 383/38 |
| 5,560,403 | A * | 10/1996 | Balteau et al. | 141/9 |
| 5,783,269 | A | 7/1998 | Heilmann et al. | |
| 5,928,213 | A | 7/1999 | Barney et al. | |
| 6,007,529 | A * | 12/1999 | Gustafsson et al. | 604/410 |
| 6,017,598 | A | 1/2000 | Kreischer et al. | |
| 6,039,719 | A * | 3/2000 | Wieslander et al. | 604/410 |
| 6,039,720 | A * | 3/2000 | Wieslander | 604/410 |
| 6,074,366 | A * | 6/2000 | Rogers et al. | 604/151 |
| 6,095,355 | A | 8/2000 | Jessen et al. | |
| 6,146,360 | A * | 11/2000 | Rogers et al. | 604/151 |
| 6,186,998 | B1 | 2/2001 | Inuzuka et al. | |
| 6,231,559 | B1 * | 5/2001 | Loretti | 604/410 |
| 6,319,243 | B1 * | 11/2001 | Becker et al. | 604/518 |
| 6,398,771 | B1 * | 6/2002 | Gustafsson et al. | 604/410 |
| 6,416,496 | B1 * | 7/2002 | Rogers et al. | 604/132 |
| 6,468,259 | B1 * | 10/2002 | Loretti et al. | 604/410 |
| 7,055,683 | B2 * | 6/2006 | Bourque et al. | 206/219 |
| 7,169,138 | B2 * | 1/2007 | Becker et al. | 604/410 |
| 7,175,614 | B2 * | 2/2007 | Gollier et al. | 604/410 |
| 7,306,095 | B1 * | 12/2007 | Bourque et al. | 206/219 |
| 7,458,741 | B2 | 12/2008 | Detwiler et al. | |
| 2001/0000042 | A1 | 3/2001 | Inuzuka et al. | |
| 2003/0036743 | A1 * | 2/2003 | Becker et al. | 604/410 |
| 2003/0040708 | A1 * | 2/2003 | Rogers et al. | 604/135 |
| 2004/0118710 | A1 * | 6/2004 | Bourque et al. | 206/219 |
| 2004/0134802 | A1 * | 7/2004 | Inoue et al. | 206/219 |
| 2007/0029001 | A1 * | 2/2007 | Trouilly et al. | 141/114 |
| 2007/0031976 | A1 * | 2/2007 | Trouilly et al. | 436/166 |
| 2007/0092579 | A1 * | 4/2007 | Trouilly et al. | 424/601 |
| 2008/0017543 | A1 | 1/2008 | Pahlberg et al. | |

FOREIGN PATENT DOCUMENTS

| | | |
|---|---|---|
| EP | 0228819 | 7/1987 |
| EP | 0811560 | 12/1987 |
| EP | 0700280 | 3/1996 |
| EP | 0739713 | 10/1996 |
| EP | 0893982 | 2/1999 |
| JP | 5-16635 | 3/1993 |
| JP | 05-016635 | 3/1993 |
| JP | 8-182739 | 7/1996 |
| JP | 2000-504956 | 4/2000 |
| JP | 2001-522655 | 11/2001 |
| WO | 9737628 | 10/1997 |
| WO | WO 98/16183 | 4/1998 |
| WO | WO 99/24086 | 5/1999 |
| WO | 0142009 | 6/2001 |
| WO | 2004047714 A1 | 6/2004 |
| WO | 2006/010411 | 2/2006 |

OTHER PUBLICATIONS

Office Action in U.S. Appl. No. 11/658,896, mailed Jan. 7, 2010.

Interview Summary in U.S. Appl. No. 11/658,896, mailed Apr. 10, 2010.

Office Action in U.S. Appl. No. 11/658,896, mailed Jul. 17, 2009.

Office Action in U.S. Appl. No. 11/658,896, mailed Feb. 6, 2009.

Written Opinion, PCT/EP2005/006474, issued Jan. 30, 2007.

International Search Report PCT/EP/2005/006475, received Aug. 30, 2005.

Written Opinion, PCT/EP2005/006475, issued Jan. 30, 2007.

Response to Office Action in U.S. Appl. No. 11/658,896, mailed Apr. 27, 2010.

Office Action in U.S. Appl. No. 11/658,896, mailed Jul. 21, 2010.

Response to Office Action in U.S. Appl. No. 11/658,896, mailed Sep. 13, 2010.

Interview Summary in U.S. Appl. No. 11/658,896, mailed Sep. 8, 2010.

Japanese Office Action, Application No. JP 2007-522932, mailed on Aug. 31, 2010.

Notice of Allowance in U.S. Appl. No. 11/658,896, issued Oct. 18, 2010.

* cited by examiner

FLEXIBLE MULTI-CHAMBER CONTAINER FOR THE PREPARATION OF MEDICAL MIXED SOLUTIONS

FIELD OF THE INVENTION

The present invention relates to a flexible multi-chamber container for the preparation of medical mixed solutions. In particularly, medical mixed solutions intended to be administered parenterally.

BACKGROUND OF THE INVENTION

Multi-chamber medical bags have been used for years for the preparation of mixed solutions. Known multi-chamber bags have different systems as separation arrangements between the chambers.

One of these containers uses breakable separation parts made of rigid, breakable materials. These have the advantages of largely universal applicability, but have disadvantages to the extent that the mixing opening has a limited cross section and undesirable particle formation may occur upon breakage of the separation arrangement. Other containers make use of peelable heatsealed welds for the separation of the fluids. These containers are flexible bags made of polymer films.

International Publication Number WO 98/10733 describes a container including three chambers for storing medical components that are mixed together to create a final medical solution. The container comprises an upper circumference region provided with means for hanging up the container and a lower circumference region provided with a port system for introducing further medical fluids and dispensing the final medical solution. The first chamber is arranged in the left side portion, the second chamber in the middle side portion and the third chamber in the right side portion of the container. The first peelable seal separating the first chamber from the second chamber as well as the second seal separating the second chamber from the third chamber are arranged in vertical directions. The triple-chamber bag is filled with components for preparing a parenteral nutrition. For administration of the parenteral nutrition the container is grasped firmly on each side and the container is firmly squeezed. The squeezing is continued until the peelable seals are fully open. After mixing the medical components the container is ready for use. An alternative method includes the step of placing the container on a flat table and rolling up the bag by hand starting from the top of the container until the peelable seals are fully open. Both opening methods result in a rapid mixing of the medical components at the same time. Both opening methods of the container do not allow in a first step mixing of the component of the first chamber with the component of the second chamber and in a second step mixing of the components of the first and second compartments with the component of third compartment.

International Publication Number WO 98/16183 discloses another flexible container with three chambers for the separated storage of the ingredients of preparations for parenteral use, namely carbohydrates within the first chamber, lipids within the second chamber, and an amino acid within the third chamber. The chambers are separated by peelable seals which can be opened sterilely from the outside. The compartments are arranged such that a rapid and complete mixing of all ingredients is possible by simply opening the connecting means. After removing the bag from an overpouch, the upper chamber is pressed by hand to mix the glucose and amino acid solutions. Following the mixing of these ingredients the lipid chamber is pressed to open the next peelable seal. The contents are mixed thoroughly by gently agitating the bag several times. The order in which the components are mixed depends on the order of pressing the compartments. Therefore, the user has to take care pressing the chambers in the correct order.

European patent document EP 0 893 982 B1 describes a container for storage of oxygen sensitive parenterally administerable agents comprising a primary container enclosed in an oxygen impermeable envelope. The container is separated into an upper chamber, a middle chamber and a lower chamber by two horizontal peelable seals. The seals can be opened by different handling techniques. The chambers and seals are arranged such that the container allows mixing of the components in a controlled order, i.e. the components of the upper and middle compartment are mixed before mixing the components of the middle and lower compartment. The designation of the chambers for the nutrients has to be done after careful consideration of both convenience and safety aspects. As such, it is preferred that either amino acid solution or lipid solution is contained in the bottom chamber, since, if the user for some reason, would be unsuccessful in correctly performing the mixture procedure, the infusion of a pure amino acid or lipid solution leaves the patient uneffected compared to the accidental infusion of pure glucose solution, which could lead to unwanted side effects, for instance, if the patient suffers from complications related to diabetes.

The most frequent complaint from customers using flexible multi-chamber bags made of polymer films is that the film is torn when the weak seal is opened. The danger of tearing the film depends on the opening technique as well as the properties of the film and the filling, sterilization and transportation process.

U.S. Pat. No. 6,017,598 suggests that peelable seals for separating the chambers should be separable with a force in the range from 5 to 20 N. If the seam is separable with a force of less than 5 N, no reliable separation of the chambers is possible, since the bond can release by itself, for example, as a result of slight shocks during transport which exert pressure on one or a plurality of chambers. At a force of 20 N, the seam can be separated only with great difficulty. There is a danger that instead of the seam, the film will tear and the bag will leak.

The two most common complaints concerning medical containers with a peelable seal are: (1) peelable seals are already opened at arrival to customer and (2) a film failure when opening peelable seals.

Since flexible containers with peelable seals of low seal strength, e.g. 5-10 N, can be damaged during manufacturing and transport, weak seals are usually protected by folding the bag. Generally, the peelable seal strength should be high enough for production and transport and still low enough to easily open the bag.

In order to simplify the opening of peelable seals, such seals have been provided with so-called rupture zones, whereby the opening force is locally reduced and the manual opening of the peelable seals is facilitated. Such seals can readily be opened by different handling techniques.

European patent document EP 0 700 280 suggests a V-shaped rupture zone. In this case, the seal opens first at the point of the V since the highest force on the seal is created there.

The container as disclosed in European patent document EP 0 893 982 comprises peelable seals having rupture zones. The rupture zones of the peelable seals are V-shaped and, therefore, comprise a point where two straight seams meet in an angle. A small or sharp angle will be easy to rupture by the user, but it will at the same time create a risk for unintentional opening when handling the container. In contrast, a very large angle will provide a seam that is difficult to open. Therefore, EP 0 893 982 suggests an angle of the seals in the rupture zone of 120° to 140°.

A first preferred opening procedure mentioned in European patent document EP 0 893 982 is to gently roll up the container from the upper side and thereby make use of the volume of the largest chamber to exert a pressure large enough to rupture the seal in its weakest point and peel apart the seam towards the sides of the container. This technique is designated as the rolling method. Another preferred way of opening the seal is to pull the front and the rear walls of the inner container apart from one another by a careful pulling motion so a rupture is formed in the weakest spot of the seal which thereby may be easy to peel apart. This technique is designated as the pulling method.

Rolling up the bag from the upper portion towards the lower portion is a safer opening method; however, most flexible containers with peelable seals are difficult to open by the rolling technique.

SUMMARY OF THE INVENTION

An object of the present invention is to provide a container that allows mixing of medical fluids in a controlled sequential order and which can be readily opened without the danger of destroying the container.

A further object of the invention is to provide a container with a peelable seal that can be readily opened without the danger of destroying the container. In particular, it is an object of the present invention to provide a flexible container with a well functioning peelable seal design, wherein the seal should be easy to open, when the seal strength is ≦40 N/30 mm; the seal should not open by slight pressure on the bag that occurs during storage and transport; the seal should not open rapidly and in one step, the seal may open in two steps—first the rupture zone and then the remaining part; and the seal should be opened by rolling as long as the seal is peelable—in this case, the seal should easily open up to seal strengths of 40 N/30 mm.

According to the invention, the flexible multi-chamber container for preparation of medical mixed solutions comprises at least three chambers separated from each other by leaktight seams. The first chamber, which is designated to be filled with a first solution, is separated from the second chamber by a first leaktight seam. The second chamber, which is designated to be filled with a second solution, is separated from the third chamber, which is designated to be filled with a third solution by a second leaktight seam. The first chamber is separated from the third chamber by a third leaktight seam.

At least a part of the first leaktight seam is provided with a separation zone to be opened for fluid transfer from the first into the second chamber. At least a part of the second leaktight seam is provided with a separation zone to be opened for fluid transfer from the second chamber into the third chamber. The entire leaktight seals may also be formed as separation zones.

According to the invention, the leaktight seams are arranged and the separation zones are formed such that, in use of the container for preparation of the medical mixed solution, the first separation and second separation zones are opened in a sequential order. Since the first zone is opened before the second separation zone is opened, the predetermined components are mixed one after another.

The arrangement of the leaktight seams, according to the invention, includes a triple-chamber container with three leaktight seams separating the chambers, but allows the use of only two leaktight seams having a separation zone. The third leaktight seam does not need a separation zone. If the third seam nevertheless would have a separation zone, this separation zone must have a higher opening strength than the separation zones of the first and second seams, respectively.

According to an embodiment of the invention, the leaktight seams are arranged and the separation zones are formed such that, in use of the container for preparation of the medical mixed solution, the first separation zone and the second separation zone are opened by exerting pressure on the container beginning from the upper portion down to the lower portion of the container. According to another embodiment, the first separation zone and the second separation zones are peelable seals that are opened by rolling up the container.

By rolling the container from the upper portion down, fluid pressure builds up in the bottom part of the container. When the pressure is high enough the peelable seals open one after the other so that the fluids are mixed. The arrangement of the peelable seals according of the invention allows a controlled mixing and reduces the problem of damage to the container.

In another embodiment, the first leaktight seal extends substantially in horizontal and vertical direction, while the second leaktight seal extends substantially in vertical direction and the third leaktight seal extends substantially in horizontal direction. Furthermore, in the embodiment, the first chamber is filled with carbohydrates containing aqueous solution, the second chamber is filled with amino acid and/or electrolytes containing aqueous solution and the third chamber is filled with lipid emulsion. It is also possible to change the assignment of said ingredients to said chambers. That is, any of the ingredients can be filled in any of the chambers. Moreover, electrolytes can also be contained in the carbohydrates containing aqueous solution instead of the amino acid containing aqueous solution.

Generally, the positions of the horizontal and vertical seals are variable. In an embodiment, however, the position of the vertical first seal is the same for all bag formats. The same position means that the distance between the vertical first seal and the border zone (lateral edge) which is nearest to said vertical seal is always the same.

The dimension should be set to get a good function when opening the bag and a balanced height of the glucose chamber. The position of the vertical second seal is set to get as high a filling grade as possible for the fat emulsion. The position for the horizontal third seal may be arranged to get a good balance for all three chambers.

Preferably, for administration of the mixed medical fluid the third chamber is provided with a port. For introducing supplementary agents according to the patient's individual requirements the first and second chambers are preferably provided with further ports.

In order to improve the controlled opening of the seams, the first and/or second peelable seals of an embodiment of the invention includes at least a rupture zone, respectively. The rupture zone of the peelable seal is curved over its whole length between straight sections of the peelable seal.

The one or more rupture zones of the peelable seal connect substantially straight sections of the peelable seal. Substantially straight means that said sections can either be absolutely straight or minimally bent with respect to the dimensions of the container. Preferably, the sections that are connected by the curved rupture zone are absolutely straight.

A peelable seal according to the present invention may contain more than one rupture zone and more than two straight sections. However, it is preferred that it contains two straight sections that are connected by one rupture zone. In the latter case, the rupture zone is, in an embodiment, located on half of the length of the peelable seal, resulting in two straight sections of equal length.

The rupture zone of the peelable seal is curved over its whole length between the straight sections. The term curved means that there are neither straight sections nor any kinks or angles within the rupture zone. A curved shape according to the present invention includes circular shapes, S-shapes and ellipsoidal shapes and irregular curved shapes, wherein circular and ellipsoidal shape mean that the curved rupture zone is formed as an arc of a circle or an arc of an ellipse. It is to be understood, in this connection, that the terms "arc of a circle" or "arc of an ellipse" are equivalent to a segment of a circle or segment of an ellipse.

In another embodiment, the curved rupture zone of the seal is formed as an arc of a circle with a radius of 5 to 75 mm, more preferably 10 to 30 mm and most preferably 20 to 25 mm, wherein the radius is measured from the center of the circle to a point on the outer edge of the seal, wherein the outer edge is the edge that is more dislodged from the central point of the circle than the inner edge.

When the curved rupture zone is formed as an arc of a circle, said arc has preferably a central angle of at least 60°, more preferably 60° to 180°, especially 90° to 150°.

It is also advantageous that the rupture zone is S-shaped, wherein a preferred S-shape is made up of two connected half circles with a radius of 5 to 75 mm, more preferably 10 to 30 mm and most preferably 20 to 25 mm. The radius is again measured from the centre of the circle to an outer edge of the seal.

The straight sections of the peelable seal can enclose an angle or the sections can be parallel to each other or in line with each other. When the straight sections form an angle, such angle is preferably from 120° to 180° and more preferably from 150° to 180°:

When the straight sections are parallel to each other, the distance (dislocation) between the straight parallel sections is preferably from 10 to 60 mm, more preferably 15 to 40 mm and most preferably 20 to 35 mm.

In a specific preferred embodiment, the curved rupture zone is formed as an arc of a circle with a central angle of 90° and the straight sections are parallel to each other.

The width of the seal can vary between the straight sections and the rupture zone. In absolute values the seal width of the straight sections is preferably from 2 to 10 mm, more preferably from 5 to 8 mm, and the seal width of the rupture zone is from 2 to 10 mm, preferably from 5 to 8 mm. In principle, the width of the straight sections can be different than the width of the rupture zone. Preferably, however, the seal width of the straight sections and the seal width of the rupture zone are the same.

The rupture zone is preferably positioned in the middle of the seal, so it can be successively opened from the middle towards the sides, since this may enable a highly reproducible opening procedure by the user from the outside of the bag. The rupture zone typically has a length of less than half the entire seal, preferably less or equal than about 40% of the seal and more preferably less than about 30% of the seal length. In a more preferred embodiment of the present invention, the length of the rupture zone amounts to 3 to 10%, more preferably 5 to 7% of the length of the peelable seal. But it can also be advantageous when length of the rupture zone is 7 to 13%. In absolute values, the length of the rupture zone is preferably 20 to 40 mm.

In an embodiment, the container is made of a flexible polymeric film having a region with a higher melt point designated as its outside and having a region with lower melt point designated as its sealing inside, which can be sealed together by means of conventional welding tools to permanent or peelable seals. It is to be understood that the inner region is intended to face the stored agent or agents and can form both permanent seals and different peelable seals when subjected to different welding conditions or operations.

It is preferred that the film is made of at least two different polymer layers wherein the inside layer is a sealant layer that is capable of forming both permanent seals and peelable seals when subjected to welding at different temperatures.

The most preferred multilayer polymer material for the manufacture of a container according to the present invention is described in European patent document EP 0 739 713 and known under the trademark Biofine™.

Another preferred multilayer polymer material can have the following structure:

The inner sealant layer is preferably based on polyolefins, such as polyethylenes or polypropylenes of various qualities which are chemically inert to the stored fluids, autoclavable, weldable and possible to recycle. The terms "polyethylenes" and "polypropylenes" are intended to include both homopolymers and copolymers having such mentioned characteristics unless otherwise is specified. Preferably, the sealant layer is based on a polyethylene homopolymer, a polyethylene copolymer, a polypropylene homopolymer, a polypropylene copolymer a polyethylene-polypropylene-copolymer and/or a mixture of polypropylene with polyethylene.

It is preferred for the inner, sealant layer to include a high amount of polyolefin, especially polypropylene, in order to benefit from its capacity of being inert towards the stored fluids and for facilitating the manufacturing of a container by means of different welding techniques. It is especially preferred that this layer can form both leaktight, but controllably rupturable, peelable seals at a predetermined temperature and permanent highly consistent seals when welding it together under different conditions such as different welding temperatures or welding pressures.

However, since many conventional polyolefins, in particular polypropylenes, often have an insufficient flexibility and a certain brittleness, it is desirable to combine them with a polymer having an elastic property. In a specific embodiment according to the present invention, it is therefore preferred to combine the polyolefin of the sealant layer with a supplementary elastomer to improve its flexibility and resilience.

The thermoplastic elastomer that can be compounded with the polyolefin in the inner sealant layer is preferably selected from the group comprising a styrene-ethylene/butylene-styrene-triblock polymer (SEBS), a styrene-ethylene/propylene-styrene-triblock polymer (SEPS), a styrene-butadiene-styrene-triblock polymer (SBS), and/or a styrene-isoprene-styrene triblock polymer (SIS).

The outer layer preferably comprises a flexible polymeric material with a high melting point that provides the material with an improved stability at the high temperatures locally reached during the welding. Suitable materials can be found among certain polyesters and copolymers thereof (copolyesters) and in particular cycloaliphatic polyesters.

There can be at least one interior layer between the outer layer and the inner sealant layer comprising a thermoplastic elastomer.

Another material that is especially suitable, for the type of containers according to the present invention, is Excel™ from McGaw Inc., a multilayered polymeric material of about 200 micrometer thickness which is described in the European patent 0 228 819. Excel™ has a multilayered structure substantially comprising: a) an inner, sealant layer facing the medical fluid consisting of a mixture of a polyethylene/ polypropylene copolymer (FINA Dypro Z 9450) and KratonB G1652 from Shell (a styrene/ethylene/butadiene/styrene (SEBS) copolymer); b) a middle, tie layer of pure KratonB G1652; and c) an outer, release layer of Ecdel™ B 9965 (or 9566 or 9967) from Eastman Chemical Co, which is a cycloaliphatic thermoplastic copolyester (a copoly(ester ether), a condensation product of the trans isomer of 1,4-dimethyl-cyclohexanedicarboxylate, of cyclohexanedimethanol and hydroxyterminated polytetramethylene glycol).

According to the present invention, other types of multilayered polymeric films, as described above, may also be used. Such other types of multilayered polymeric films are made of at least two different polymer layers, wherein the inside layer is a sealant layer that is capable of forming both permanent seals and peelable seals—which are described in European patent document EP 0 893 982, European patent document EP 0 700 280 and International Publication Number WO 01/42009, as well as methods for their production and methods for welding peelable seals.

The container or bag with peelable seals as described above may be enclosed in an overpouch with a high oxygen barrier. Said overpouch film is preferably a multi-layer structure including PET, a thin glass coating and polypropylene. Suitable overpouches are for example described in European patent document EP 0 893 982. An oxygen absorber may be placed between the container and the overpouch.

Generally, hot bar heat sealing or impulse heat sealing processes may be used for producing permanent and peelable seals according to the invention.

Suitable peelable seal welding temperatures for the above mentioned Biofine™ films are in the range of 122 to 130° C. Such seals are suitably leaktight after being subjected to conventional mechanical package tests and are objectively easy to open. They are also relatively easy to open after the container has been subjected to steam sterilization. Suitable welding temperatures for forming permanent seals with Biofine™ film are in the range of 130 to 160° C.

When Excel™ is used as multilayer film material for the manufacture of containers, the temperature for welding peelable seals is 113 to 120° C. and the temperature for welding permanent seals is 130 to 160° C.

DETAILED DESCRIPTION OF THE DRAWINGS

In the following exemplary embodiments a device in accordance with the present invention is explained in greater detail by reference to the figures.

Figure 1:
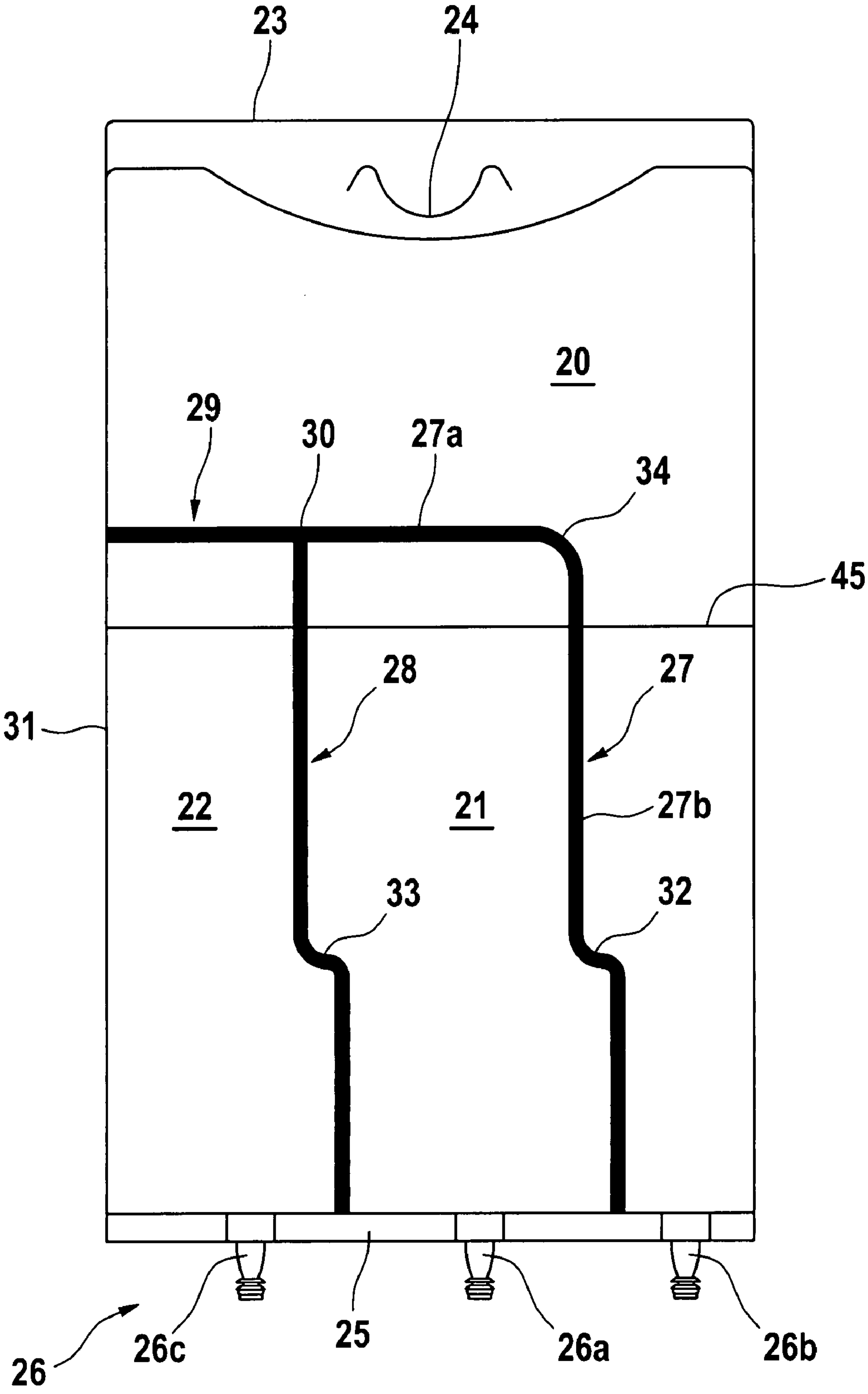
FIG. 1 schematically illustrates a plan view of the container according to a specific embodiment of the present invention.
Figure 3:
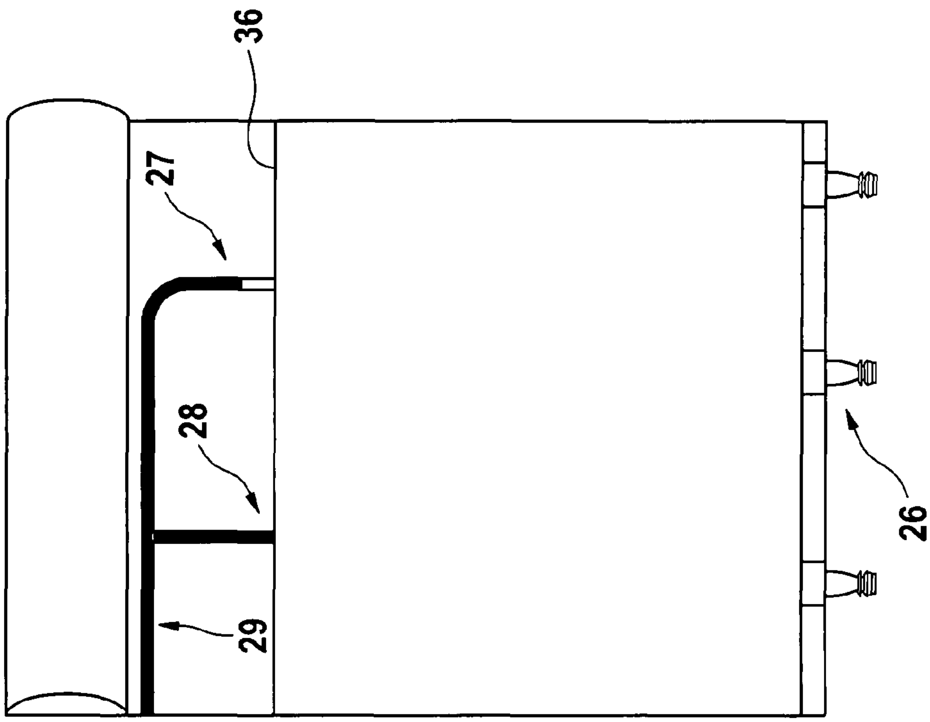
FIG. 3 illustrates the container including the mixed medical fluid.
Figure 2:
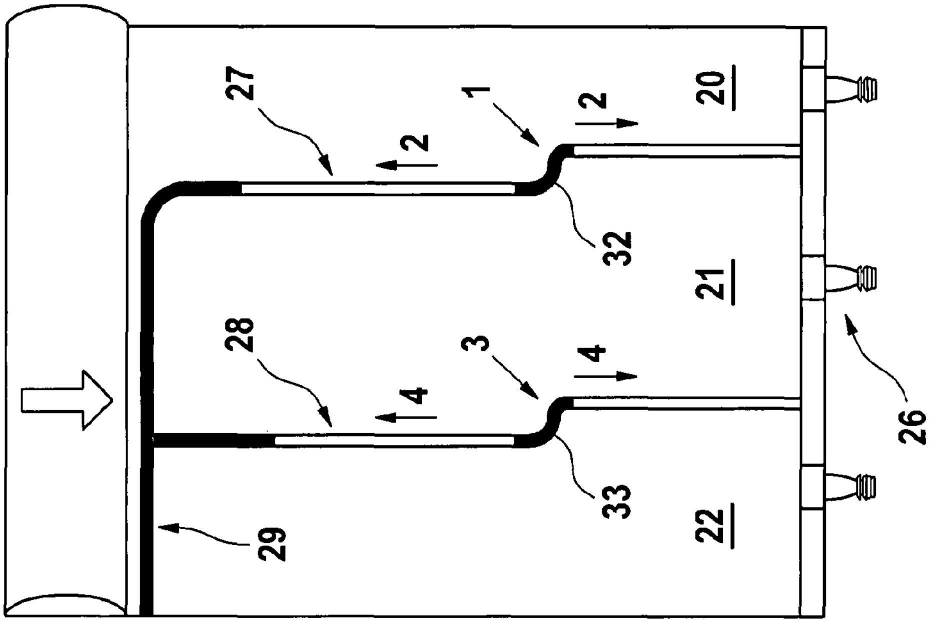
FIG. 2 illustrates the opening of the peelable seals by rolling up the container.

Referring now to FIG. 1, an embodiment of the invention is illustrated. The container includes a first chamber 20, a second chamber 21, and a third chamber 22. The three chambers are filled with three different parenterally administrable nutrients in fluid form which, just before their administration to the patient, are homogeneously mixed together to form a total parenteral nutrition (TPN) solution. In the specific embodiment, the first chamber 20 is filled with carbohydrates containing aqueous solution, i.e. glucose; the second chamber 21 is filled with electrolytes and/or amino acid containing aqueous solution; and the third chamber 22 with lipid emulsion, i.e. the fat component. The fluid level of the solutions is designated with the reference number 45. It should be noted that although three chambers are present in the embodiment, more chambers can be used. It should also be noted that the contents of the three chambers might vary and that other alternative contents are possible as well. According to the invention it is possible to change the assignment of said ingredients to said chambers. That is, any of the ingredients can be filled in any of the chambers. In another embodiment chamber 22 contains amino acid solution and chamber 21 contains lipid emulsion. Moreover, electrolytes may also be contained in the carbohydrates containing aqueous solution.

In an embodiment of the invention, the flexible container is formed from a blown film of 280 or 320 mm width such that only the upper border zone and the lower border zone are sealed together. The upper border zone 23 has a suspension arrangement 24 in the form of an opening so that the container may be hung for bedside administration of the ingredient mixture. The lower border zone 25 has an administration port system 26 for dispensing the medical mixed fluid and introducing supplementary agents according to the patient's requirements.

The administration port system 26 comprises three ports inserted into the lower border zone 25 of the container. All ports may be used for filling the chambers. Moreover, port **26*a* is also provided as an additive injection port for injecting compatible additives directly into the chamber/chambers using a needle or syringe under aseptic conditions. Port 26*b* is also provided as an infusion port for administration of the product to the patient. Port 26*c*** is, in this embodiment, closed with a cap after filling the chamber.

The type of port that should be connected to the different chambers depends on the arrangement of the departments. In the embodiment, port **26*a* is inserted into the lower border zone below the second chamber 21, port 26*b* below the first chamber 20, and port 26*c* below the third chamber 22. In another embodiment, the additive port 26*a* is below third chamber 22**. Ports belong to the prior art and are described, e.g. in European patent document EP-A-0 811 560.

The container is made of a multi-layer polypropylene-based film, e.g. as described in European patent document EP-A-0 228 819 or European patent document EP-A-O 739 713, that can form both peelable seals and permanent seals using hot bar heat sealing or impulse heat sealing processes.

The container as a primary bag is enclosed in an overpouch with high oxygen barrier. The overpouch film is a multi-layer structure including PET, a thin glass coating and polypropylene. The thin glass coating provides the oxygen barrier properties. An oxygen absorber is placed between the primary and secondary bags.

The first chamber 20 has a larger volume than the second and third chambers 21, 22, respectively. The first chamber 20 is arranged in the horizontal upper portion as well as in the vertical right side portion of the container. The upper portion extends about ⅓ of the total length between the upper and lower border zones and the right side portion extends about ⅓ of the total width of the container between the right and left border zones. The second chamber 21 is arranged in the vertical middle portion of the container below the upper part of the first chamber. The middle portion extends about ⅓ of the total width of the container. The third chamber 22 is arranged in the vertical left side portion of the container below the upper part of the first chamber. The left side portion extends about ⅓ of the total width of the container.

The three chambers of the container are separated by three highly leaktight welded seams. The first chamber 20 is separated from the second chamber 21 by a first leaktight seam 27 ("seal 1"). The second chamber 21 is separated from the third chamber 22 by a second leaktight seam 28 ("seal 2"). The first chamber 20 is separated from the third chamber 22 by a third leaktight seam 29.

The first seam 27 has a horizontal extending portion 27*a* as well as a vertical extending portion 27*b*, whereas the second seam 28 has a vertical extending portion and the third seam 29 has a horizontal extending portion only. The first, second and third seams have a common upper end 30.

In the embodiment, beginning from the left border zone 31, the horizontal third seam 29 extends about ⅓ of the width of the container at about ⅓ of the length of the container between the first and third chambers. Beginning from the end of the third seam 29, the second seam 28 extends in vertical direction to the lower border zone 25 of the container separating the second and third chambers. Also beginning from the end of the third seam 29, the horizontal portion 27*a* of the first seam 27 extends about ⅓ of the width of the container at about ⅓ of the length of the container, and the vertical portion 27*b* of the first seam extends from the end of the horizontal portion in vertical direction to the lower border zone 25 separating the first and second chambers.

The first and second seams are formed as peelable seals comprising rupture zones 32, 33. The third seam 29 is preferably also formed as a peelable seal, wherein it has an opening strength that is equal to or higher than the opening strength of the first and second seals, respectively. Seam 29 may, however, also be formed as a permanent seal.

The rupture zones of the peelable seals are described in detail in FIGS. 4 to 9.

In the embodiment, the first peelable seal 27 includes a first rupture zone 32 and the second peelable seal 28 includes a second rupture zone 33—in order to avoid ripping the film when opening the seals. The curved opening zones are formed such that the seals slowly open in two steps, i.e. in a first step at the opening zone and in a second step at their other portions.

The transition zone 34, between the horizontal and vertical portions 27*a*, 27*b* of the first seam 27, is also formed as a rupture zone 34, but the transition rupture zone has preferably a larger radius of curvature than the other rupture zone 32 of the first peelable seal 27. A larger radius results generally in a higher opening force of the peelable seal, so that generally rupture zone 32 opens before rupture zone 34. The function of the bag is, however, not affected if rupture zone 34 opens before zone 32 as long as seal 27*b* opens all the way to the bottom of the bag before rupture zone 33 opens.

The rupture zones of both seals can be arranged anywhere from the lower border zone up to the fluid level. A preferred placement is at least 50 mm above the border zone 25 (bottom seal) and at least 50 mm below the fluid level of a mixed bag. The optimal placement of the rupture zone is, however, approximately halfway between the lower border zone and the fluid level.

The flexible container, according to the present invention, is easy to handle in a controlled manner. In order to mix the solutions for preparation of the parenteral fluid, the container is rolled up from the upper border zone towards the lower border zone.

By rolling the container up fluid pressure is built up in the chambers. When the pressure is high enough the first peelable seal opens at the curved rupture zone, i.e. the zone with the smallest radius. By further rolling the container up the fluid pressure further increases and the other portions of the first peelable seal continue to open starting from the curved rupture in both directions. The seal opens down to the lower border zone and up to the fluid level. When the fluid level 45 is reached there is no more pressure on the seal and the seal will not further open. After opening the first seal, the second seal is opened at the curved rupture zone. In the same way as for the first seal, the seal opening of the second seal propagates up and down. Therefore, the first and second solutions of the first and second chambers, respectively, are mixed in a first step, and the mixture of the first and second solutions and the third solution are mixed in a second step. This is guaranteed by having preferably higher weak seal strength for the third seal with respect to the second and first seal, respectively. If, nevertheless, the third and first seals have the same seal strength, the curved rupture zone of the first seal guarantees the opening of the first seal before the second seal.

Even if the horizontal portions of the seals have a lower seal strength then the vertical portions, the transition rupture zone 34 of the first seal guarantees the opening of the first seal 27 before the second seal 28.

FIGS. 6 to 9 illustrate preferred shapes of peelable seals including a rupture zone, which may be used in the container of FIG. 1 as peelable seals 27 and 28. Also, the prior art peelable seal of FIGS. 4 and 5 may be used, but not as advantageously as the seals of FIGS. 6 to 9. The practice has shown that a straight peelable seal (FIG. 4—shape A) is limited to a low seal strength to remain easily openable. Seals B (FIG. 5, reference example according to the state of the art of European patent document EP 0 893 982) and C (FIG. 6) can be easily opened at higher seal strengths while inventive seal shapes D and E (FIGS. 7 and 8) can be easily opened even at high seal strengths. A seal that is easily opened at high seal strengths is preferred from a manufacturing point of view since a high seal strength enhances processability and transportation properties. An infusion bag with a seal strength as low as reference example A requires some kind of support of the seal during transportation, i.e. a fold along the seal line. A comparison of seals C and D has shown that seals of a higher strength can be opened by decreasing the radius of the rupture zone and at the same time adjusting one of the straight sections of the peelable seal parallel to the other creating a gap.

Figure 4:
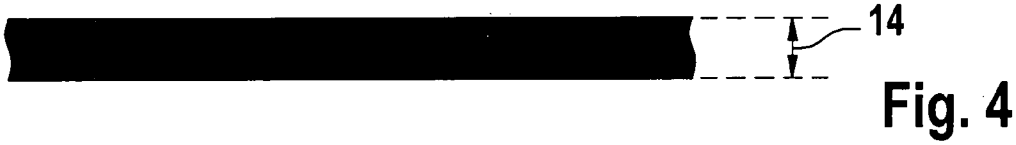
FIG. 4 illustrates a straight seal according to the prior art.

FIG. 4 shows a straight peelable seal according to the state of the art which has no rupture zone (seal type A). The seal width 14 is 20 mm.

Figure 5:
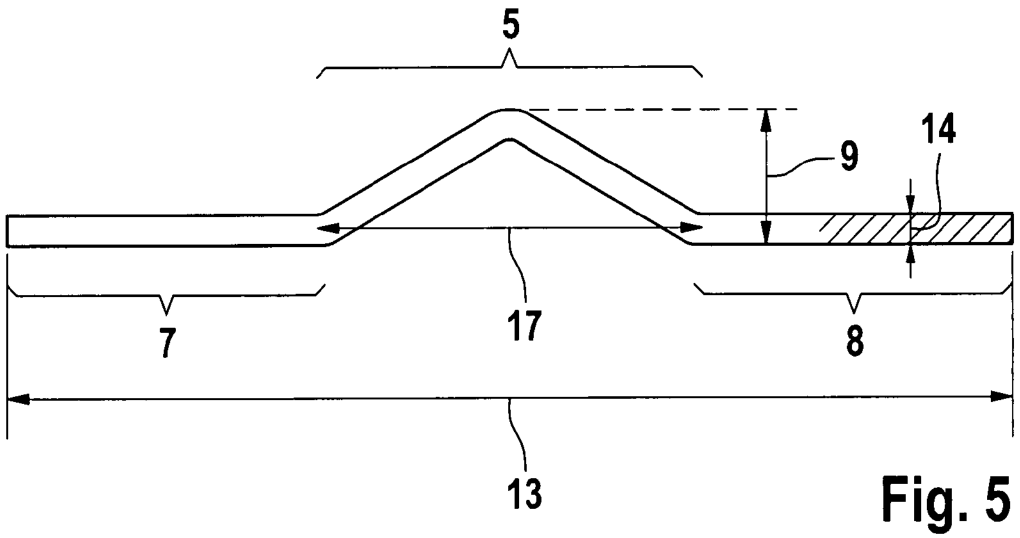
FIG. 5 illustrates a seal with a V-shaped rupture zone according to the prior art.

FIG. 5 shows a peelable seal with two straight sections 7, 8 and a V-shaped rupture zone 5 according to the state of the art (seal type B). The seal width 14 is 5 mm, the width of the rupture zone 17 is 150 mm and the height 9 of the rupture zone is 30 mm. Reference symbol 13 stands for the total length of the seal.

Figure 6:
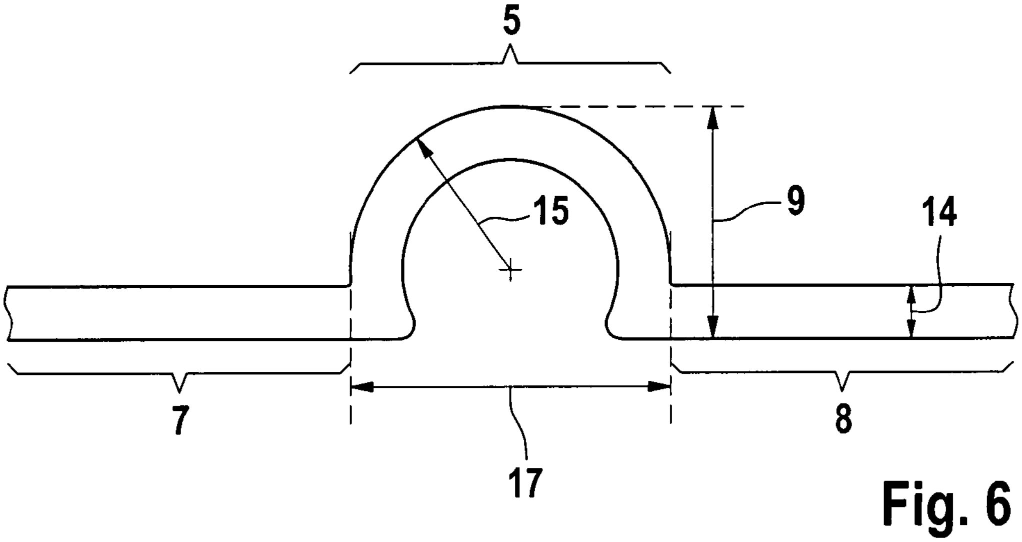
FIG. 6 illustrates a first preferred embodiment of the rupture zone of the first and second seals, respectively.

FIG. 6 shows in detail a preferred shape of a peelable seal according to the present invention (seal type C) with two straight sections 7, 8 and a rupture zone 5. The seal width 14 is 7 mm and the radius 15 is 90 mm. The width of the rupture zone 17 is 145 mm and the height of the rupture zone 9 is 43 mm.

Figure 7:
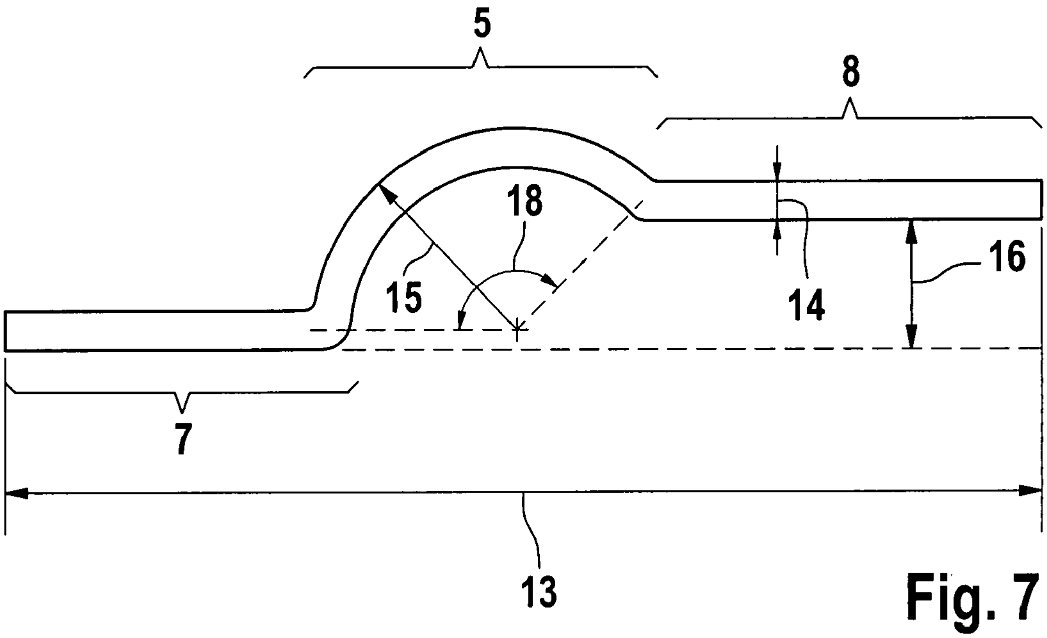
FIG. 7 illustrates a second preferred embodiment of the rupture zone of the first and second seals, respectively.

FIG. 7 shows another preferred shape of a peelable seal (seal type D), wherein the rupture zone 5 is formed as an arc of a circle with a central angle 18 of 145°. The radius 15 is 20 mm. The straight sections 7, 8 are located parallel to each other with a dislocation 16 of 15 mm. The seal width 14 is 7 mm. Reference symbol 13 stands for the total length of the seal.

Figure 8:
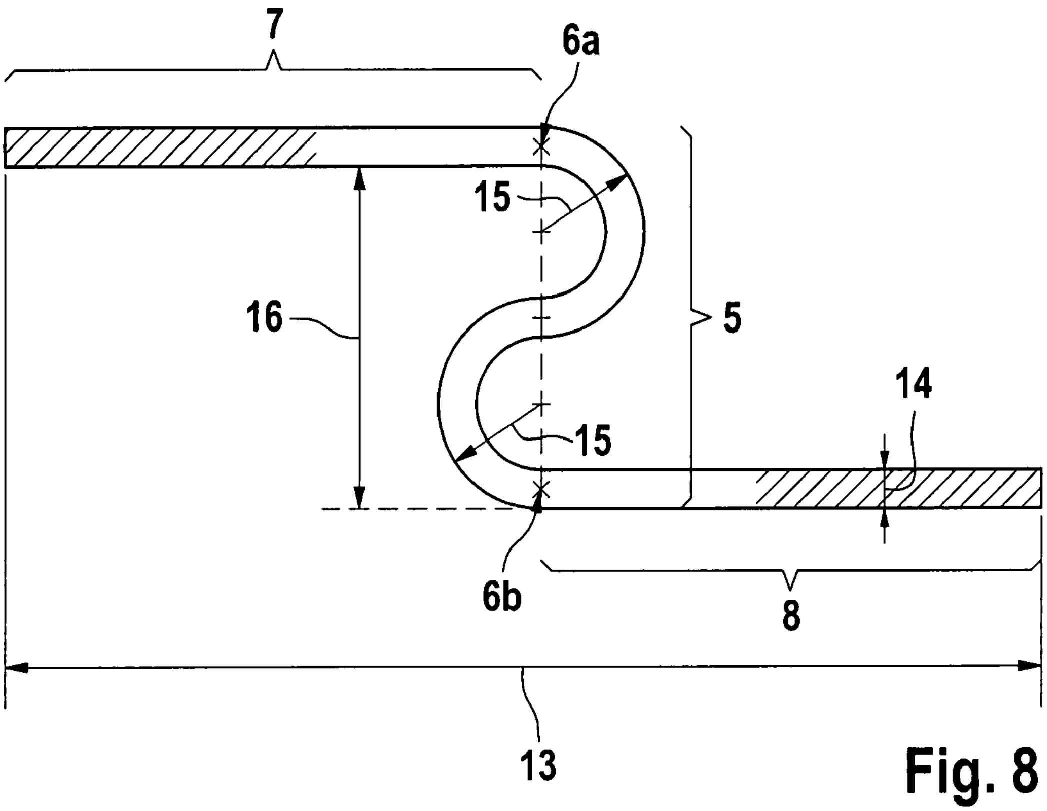
FIG. 8 illustrates a third embodiment of the rupture zone of the first and second seals, respectively.

FIG. 8 shows another preferred shape of a peelable according to the present invention (seal type E) with a rupture zone 5 that is S-shaped between end points 6*a* and 6*b*. The S-shaped rupture zone is formed from two half circles with a radius 15 of 15 mm. The straight sections of the seal 7, 8 are located parallel to each other with a dislocation 16 of 60 mm. The seal width 14 is 7 mm. Reference symbol 13 stands for the total length of the seal.

Figure 9:
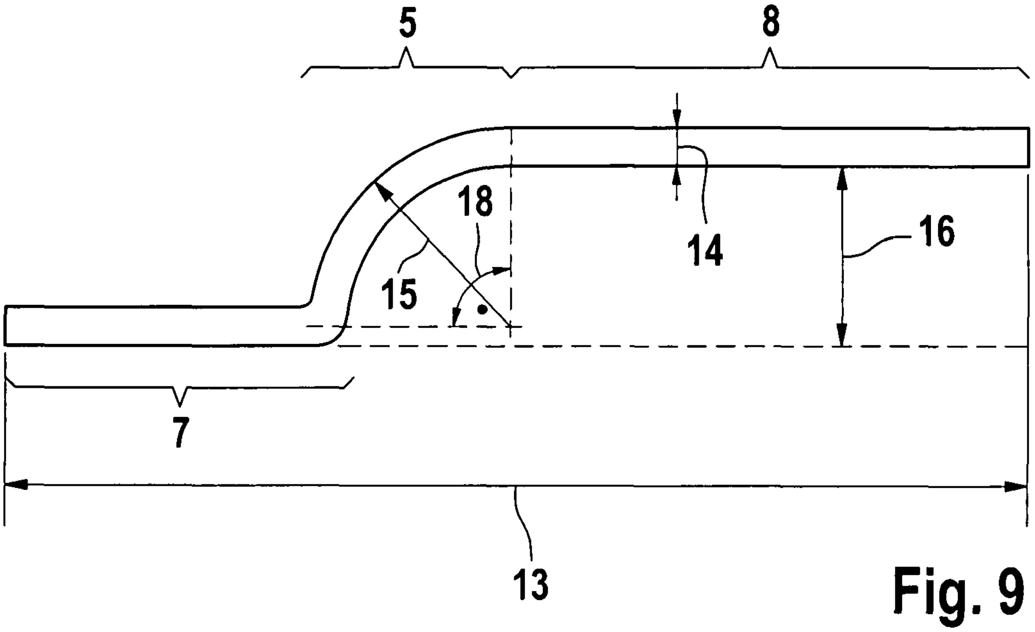
FIG. 9 illustrates a further embodiment of the rupture zone of the first and second seals, respectively.

FIG. 9 shows another preferred shape of a peelable seal (seal type F), wherein the rupture zone 5 is formed as an arc of a circle with a central angle 18 of 90°. The radius 15 is 20 mm. The straight sections 7, 8 are located parallel to each other with a dislocation 16 of 20 mm. The seal width 14 is 7 mm. Reference symbol 13 stands for the total length of the seal.

EXAMPLES

It is to be understood that the following examples are illustrative and do not limit the scope and idea of the invention.

A) General Procedure for Forming a Container According to FIG. 1

Containers as shown in FIG. 1 were manufactured from a blown tube film (Biofine™) based on polyolefins. The peelable seals were welded at different temperatures from 122 to 128° C. to achieve different weld strengths, 3 seconds and 4 bar using the hot bar technique. The rupture zone (peak) was placed at 40 mm, 100 mm and 160 mm from the bottom weld. The total bag length was 400 mm, the bag width was 280 mm (FIG. 11) and the total length of the peelable seals was 260 mm. The total fluid volume in the bag was 1500 ml.

Permanent seals were impulse welded.

B) Performed Tests

Bags according to FIG. 1 were manufactured according to the above procedure with different peak positions. Peelable seals were welded at 122, 124, 126 and 128° C. Every sample group contained 10 bags. The bags were not autoclaved. The following tests have been performed on each sample group.

Tensile Test

Figure 10:
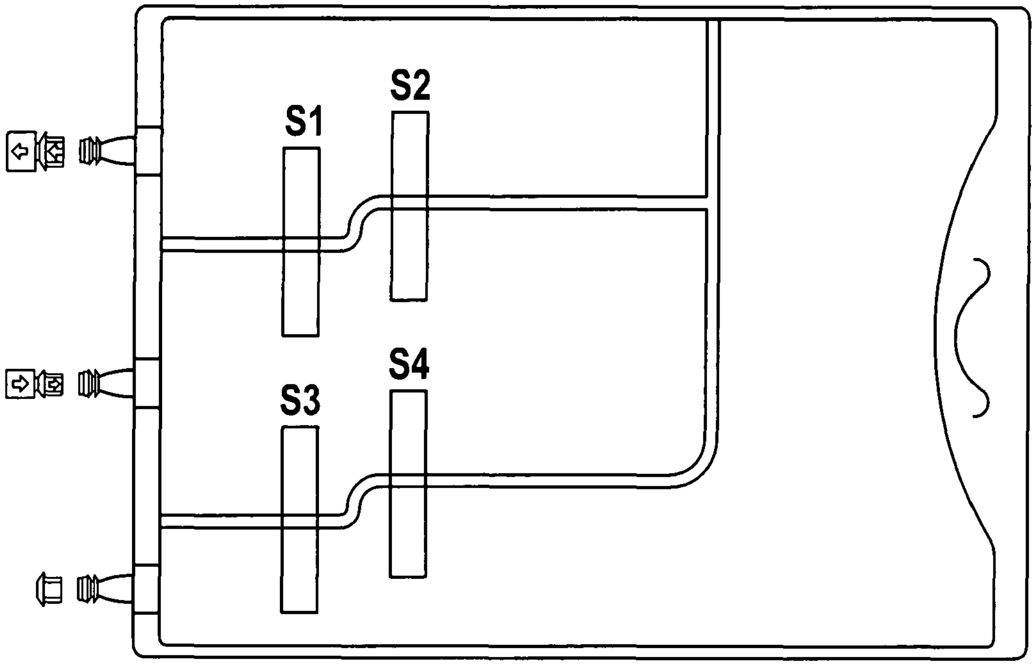
FIG. 10 is an illustration of sampling that shows peelable seal-positions S1, S2, S3 and S4 for tensile testing with a container according to FIG. 1 (see Example).

Tensile tests were performed on 30 mm wide strips using an Instron tensile tester. Test strips were taken from position S1, S2, S3 and S4 (see FIG. 10 for positions). Initial grip separation was set to 50 mm. Test speed was set to 500 mm/min. Maximum force was measured.

The seal strength was measured on 3 bags.

Burst Test

No restrain plates were used. The pressure was registered directly inside the bag using a pressure sensor. Incoming pressure was set to 0.3 bars. The weak seals were opened in peak direction, i.e. seal 1 was opened before seal 2.

Burst test was performed on 3 bags.

Manual Opening of Bags

The peelable seals are manually opened by the roll method. The degree of difficulty was rated 1-5 according to below definition.

1=Very easy

2=Easy

3=Some resistance but no problem to open

4=High resistance but possible to open with big effort

5=Not possible to open

Manual opening was performed on 4 bags.

C) Test Results for Different Peak Positions

Peak Position 40 mm

In the table below the peelable seal strengths, burst values and ratings for manual opening at different welding temperatures are shown.

| Welding | Peelable seal strength | Burst value (bar) | | Rating for manual opening | |
|---|---|---|---|---|---|
| temperature (° C.) | (N/30 mm) | Seal 1 | Seal 2 | Seal 1 | Seal 2 |
| 122 | 16 | 0.17 | 0.12 | 1.5 | 1.9 |
| 124 | 21 | 0.20 | 0.14 | 2.3 | 3.0 |
| 126 | 26 | 0.25 | 0.17 | 3.0 | 3.3 |
| 128 | 37 | 0.32 | 0.28 | 3.5 | 4.7 |
| 130 | 46 | >0.30 | >0.30 | 5.0 | 5.0 |

Peak Position 100 mm

In the table below the peelable seal strengths, burst values and ratings for manual opening at different welding temperatures are shown.

| Welding | Peelable seal strength | Burst value (bar) | | Rating for manual opening | |
|---|---|---|---|---|---|
| temperature (° C.) | (N/30 mm) | Seal 1 | Seal 2 | Seal 1 | Seal 2 |
| 122 | 16 | 0.12 | 0.09 | 1.0 | 1.0 |
| 124 | 21 | 0.16 | 0.11 | 1.8 | 2.0 |
| 126 | 27 | 0.19 | 0.12 | 1.8 | 2.0 |
| 128 | 37 | 0.28 | 0.16 | 2.5 | 2.7 |
| 130 | 45 | >0.30 | >0.30 | 4.0 | 4.0 |

Peak Position 160 mm

In the table below the peelable seal strengths, burst values and ratings for manual opening at different welding temperatures are shown.

| Welding | Peelable seal strength | Burst value (bar) | | Rating for manual opening | |
|---|---|---|---|---|---|
| temperature (° C.) | (N/30 mm) | Seal 1 | Seal 2 | Seal 1 | Seal 2 |
| 122 | 16 | 0.14 | 0.09 | 1.3 | 2.3 |
| 124 | 21 | 0.17 | 0.10 | 2.0 | 3.5 |
| 126 | 28 | 0.21 | 0.13 | 2.4 | 4.3 |
| 128 | 37 | 0.28 | 0.19 | 3.0 | 5.0 |
| 130 | 45 | >0.30 | >0.30 | 5.0 | 5.0 |

Comparison and Discussion

In the table below a summary for peak positions 40, 100 and 160 mm is shown. The degrees of difficulty for manual opening of the bag are listed at different seal strengths.

| Welding temperature (° C.) | Peelable seal strength (N/15 mm) | Rating for manual opening with peak position 40 mm | | Rating for manual opening with peak position 100 mm | | Rating for manual opening with peak position 160 mm | |
|---|---|---|---|---|---|---|---|
| | | Seal 1 | Seal 2 | Seal 1 | Seal 2 | Seal 1 | Seal 2 |
| 122 | 16 | 1.5 | 1.9 | 1.0 | 1.0 | 1.3 | 2.3 |
| 124 | 21 | 2.3 | 3.0 | 1.8 | 2.0 | 2.0 | 3.5 |
| 126 | 27 | 3.0 | 3.3 | 1.8 | 2.0 | 2.4 | 4.3 |
| 128 | 37 | 3.5 | 4.7 | 2.5 | 2.7 | 3.0 | 5.0 |
| 130 | 45 | 5.0 | 5.0 | 4.0 | 4.0 | 5.0 | 5.0 |

The results show that peelable seals with a high peak position are easier to open than peelable seals with a low peak position. When the peak position is too high, close to the fluid level of the mixed bag as in peak position 160 mm seal 2 the seal becomes more difficult to open. A comparison of the peak positions evaluated in this example shows that a peak position of 100 mm is the preferred position.

D) Further Preferred Bag Dimensions

Figure 11:
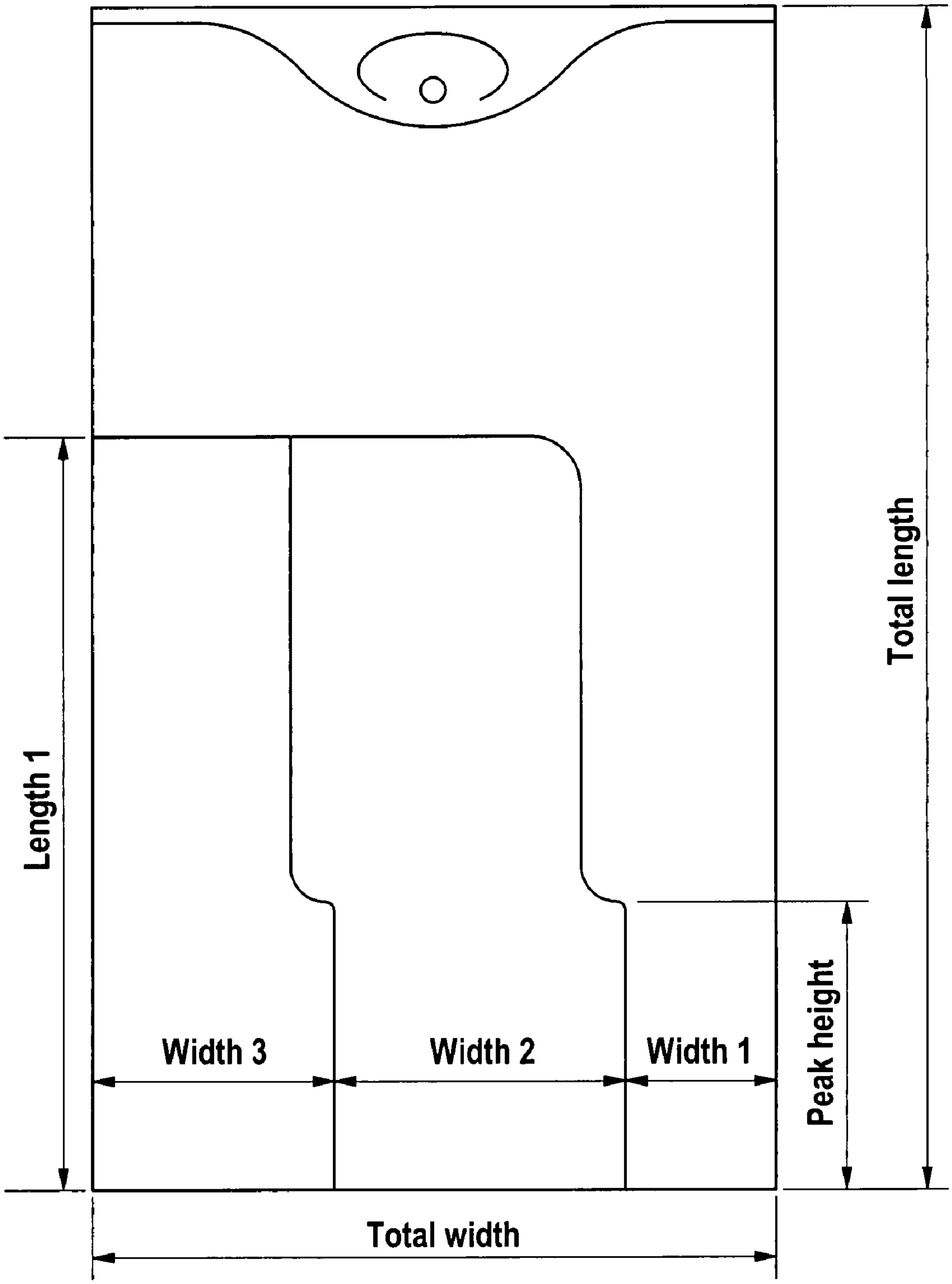
FIG. 11 is an overview of the bag dimensions and their designation.

In the table below, further preferred bag dimensions according to FIG. 11 are listed

| | Bag format | | | |
|---|---|---|---|---|
| | A | B | C | D |
| Total length (mm) | 335 | 385 | 445 | 445 |
| Length 1 (mm) | 210 | 240 | 234 | 279 |
| Total width (mm) | 280 | 280 | 320 | 320 |
| Width 1 (mm) | 60 | 60 | 60 | 60 |
| Width 2 (mm) | 114 | 109 | 123 | 133 |
| Width 3 (mm) | 90 | 95 | 121 | 111 |
| Peak height (mm) | 60 | 100 | 100 | 100 |

In the above embodiments width 1, which is the distance between the vertical first seal and the nearest border zone (lateral edge), is always the same.

The invention claimed is:

1. A flexible multi-chamber container for preparation of medical mixed solutions, comprising:

a first chamber configured to receive a first solution;

a second chamber configured to receive a second solution;

a third chamber configured to receive a third solution;

a first leaktight seam separating the first chamber from the second chamber;

a second leaktight seam separating the second chamber from the third chamber; and a third leaktight seam separating the first chamber from the third chamber;

wherein at least a part of the first leaktight seam includes a first separation zone configured to open to allow for fluid transfer from the first chamber into the second chamber and at least a part of the second leaktight seam includes a second separation zone configured to open to allow for fluid transfer from the second chamber into the third chamber, wherein, in preparation of the medical mixed solution, the first separation zone is configured to open before the second separation zone opens, wherein the first leaktight seam includes horizontal and vertical portions, and the first separation zone is arranged in the vertical portion of the first leaktight seam, wherein the first separation zone and the second separation zone are configured to open by exerting pressure on the container beginning from an upper portion of the first chamber down to a lower portion of the second and third chambers, wherein the first chamber is L-shaped such that the first chamber is arranged in the upper portion and adjacent to both a horizontal side and a vertical side of the second chamber and adjacent to a horizontal side of the third chamber of the container.

2. The multi-chamber container according to claim 1, wherein the first separation zone and the second separation zone open by rolling up the container.

3. The multi-chamber container according to claim 1, wherein the first separation zone is a first peelable seal and the second separation zone is a second peelable seal.

4. The multi-chamber container according to claim 1, wherein the second leaktight seam extends substantially in a vertical direction.

5. The multi-chamber container according to claim 1, wherein the third leaktight seam extends substantially in a horizontal direction.

6. The multi-chamber container according to claim 1, wherein the first leaktight seam, second leaktight seam and third leaktight seam have a common upper end.

7. The multi-chamber container according to claim 1, wherein the first chamber is arranged in a right side portion of the container.

8. The multi-chamber container according to claim 1, wherein the second chamber is arranged in a middle portion of the container below the first chamber.

9. The multi-chamber container according to claim 1, wherein the third chamber is arranged in a left side portion of the container below the first chamber.

10. The multi-chamber container according to claim 1, wherein the first chamber has a larger volume than the second chamber or the third chamber, respectively.

11. The multi-chamber container according to claim 1, wherein the first chamber is filled with carbohydrates and/or electrolytes containing aqueous solution.

12. The multi-chamber container according to claim 1, wherein the second chamber is filled with amino acid containing aqueous solution.

13. The multi-chamber container according to claim 1, wherein the third chamber is filled with lipid emulsion.

14. The multi-chamber container according to claim 1, wherein the first chamber, the second chamber and the third chamber are provided with a port system for dispensing a medical mixed fluid made from a first liquid, a second liquid and a third liquid and/or for introducing supplementary agents.

15. The multi-chamber container according to claim 1, wherein the container comprises a polymeric film, the container including a first region forming an outside area and a second region forming a sealing inside area, the first region having a higher melting point than the second region, wherein the second region forming the sealing inside area is structured to form both permanent seals and peelable seals when subjected to different welding conditions.

16. The multi-chamber container according to claim 1, wherein the container comprises a polymeric film including at least two layers including an inside layer that is a sealant layer structured to form both permanent seals and peelable seals when subjected to welding at different temperatures.

17. The multi-chamber container according to claim 1, wherein the first separation zone is the entire first leaktight seam.

18. The multi-chamber container according to claim 1, wherein an inner sealant top layer and an inner sealant bottom layer are directly sealed together at the location of the leaktight seams.

19. The multi-chamber container according to claim 1, wherein exerting pressure comprises rolling the container.

20. The multi-chamber container according to claim 1, wherein the third leaktight seam is permanent.

21. A flexible multi-chamber container for preparation of medical mixed solutions, comprising:

- a first chamber configured to receive a first solution;
- a second chamber configured to receive a second solution;
- a third chamber configured to receive a third solution;
- a first leaktight seam separating the first chamber from the second chamber;
- a second leaktight seam separating the second chamber from the third chamber; and
- a third leaktight seam separating the first chamber from the third chamber;
- wherein at least a part of the first leaktight seam includes a first peelable seal configured to open to allow for fluid transfer from the first chamber into the second chamber and at least a part of the second leaktight seam includes a second peelable seal configured to open to allow for fluid transfer from the second chamber into the third chamber, and
- wherein at least one of the first peelable seal and the second peelable seal comprises a curved rupture zone extending from a first substantially straight section to a second substantially straight section, the rupture zone curving its entire length, and the first and second substantially straight sections being parallel to each other,
- wherein the first chamber is L-shaped such that the first chamber is arranged in the upper portion and adjacent to both a horizontal side and a vertical side of the second chamber and adjacent to a horizontal side of the third chamber of the container.

22. The multi-chamber container according to claim 21, wherein the curved rupture zone forms an arc of a circle with a radius of 5 to 75 mm, wherein the radius extends from the center point of the circle to a point on an outer edge of the at least one of the first peelable seal and the second peelable seal.

23. The multi-chamber container according to claim 21, wherein the curved rupture zone is an arc of a circle with a radius of 10 to 30 mm.

24. The multi-chamber container according to claim 21, wherein the curved rupture zone is an arc of a circle with a radius of 20 to 25 mm.

25. The multi-chamber container according to claim 21, wherein the arc of the circle has a central angle of at least 60°.

26. The multi-chamber container according to claim 21, wherein the arc of the circle has a central angle of 60° to 180°.

27. The multi-chamber container according to claim 21, wherein the curved rupture zone is S-shaped, having no straight or pointed portions.

28. The multi-chamber container according to claim 21, wherein the at least two substantially straight sections are offset laterally by a distance of about 5 to 75 mm.

29. The multi-chamber container according to claim 21, wherein the seal width of the at least two substantially straight sections and the rupture zone is from 2 to 10 mm.

30. A flexible multi-chamber container for preparation of medical mixed solutions, comprising:

- a first chamber configured to receive a first solution;
- a second chamber configured to receive a second solution;
- a third chamber configured to receive a third solution;
- a first leaktight seam separating the first chamber from the second chamber;
- a second leaktight seam separating the second chamber from the third chamber; and
- a third leaktight seam separating the first chamber from the third chamber;
- wherein at least a part of the first leaktight seam includes a first separation zone configured to open to allow for fluid transfer from the first chamber into the second chamber and at least a part of the second leaktight seam includes a second separation zone configured to open to allow for fluid transfer from the second chamber into the third chamber,
- wherein, in preparation of the medical mixed solution, the first separation zone is configured to open before the second separation zone opens, and
- wherein the container is configured to allow the first solution, the second solution, and the third solution to be homogeneously mixed together,
- wherein the first leaktight seam extends substantially in horizontal and vertical directions and is configured to open in both horizontal and vertical directions,
- wherein the first separation zone and the second separation zone are configured to open by exerting pressure on the container beginning from an upper portion of the first chamber down to a lower portion of the second and third chambers,
- wherein the first chamber is arranged in the upper portion and to the right side of the second and third chambers of the container, and a bottom portion of the container comprises a port.

* * * * *